(12) United States Patent
Lacey et al.

(10) Patent No.: US 6,370,946 B1
(45) Date of Patent: Apr. 16, 2002

(54) HIGH TEMPERATURE DIESEL DEPOSIT TESTER

(75) Inventors: Paul Lacey; Jose De La Cruz; Eliazar H. Saucedo; Jack Russell Compton, all of San Antonio, TX (US)

(73) Assignee: Southwest Research Institute, San Antonio, TX (US)

( * ) Notice: Subject to any disclaimer, the term of this patent is extended or adjusted under 35 U.S.C. 154(b) by 0 days.

(21) Appl. No.: 09/563,170

(22) Filed: May 2, 2000

(51) Int. Cl.$^7$ ............................ G01N 11/00; G01N 5/00
(52) U.S. Cl. ...................... 73/61.62; 73/61.71
(58) Field of Search .............. 73/61.62, 61.63, 73/61.71, 61.72

(56) References Cited

U.S. PATENT DOCUMENTS

| | | | |
|---|---|---|---|
| 3,059,467 A | 10/1962 | Meguerian | 73/61 |
| 3,108,468 A | * 10/1963 | Mickel | 73/61.62 |
| 3,318,668 A | 5/1967 | Fabuss et al. | 23/253 |
| 3,438,248 A | 4/1969 | Taylor et al. | |
| 5,036,699 A | * 8/1991 | Fikentscher et al. | 73/61.62 |
| 5,101,658 A | * 4/1992 | Wilson, III et al. | 73/61.62 |
| 5,299,499 A | * 4/1994 | Hardy et al. | 73/61.62 |
| 5,492,005 A | * 2/1996 | Homan et al. | 73/61.62 |
| 5,693,874 A | 12/1997 | DeLaCruz et al. | |

FOREIGN PATENT DOCUMENTS

SU   129872   * 1/1959   ............... 73/61.62

* cited by examiner

*Primary Examiner*—Hezron Williams
*Assistant Examiner*—Michael Cygan
(74) *Attorney, Agent, or Firm*—Gunn, Lee & Keeling

(57) ABSTRACT

A method and apparatus for determining the propensity of fuel materials to leave deposits in compression ignition engines is disclosed. The apparatus consists of a closed chamber fitted with conduits to supply fuel composition, air, and other test fluids to its interior, and arranged to contain or substantially contain a substrate. Substrate is placed in the chamber to provide interaction between a fluid passing through and the substrate. Substrate may be a monolithic machined element or a collection of discrete bodies. The chamber conduits are connected to at least two metering devices, one controlling fuel and one air flow, whereby the substrate is exposed to measured quantities of fuel compositions and air. Heating devices are in thermal communication with the substrate and the source of air provided to the chamber, thus providing a method of controlling the temperature of the substrate and air flowing through the chamber. The propensity of a fuel composition to form deposits in an engine is determined by alternatively dispersing fuel composition and hot air upon the heated substrate then determining the mass of the deposits left on the substrate.

8 Claims, 10 Drawing Sheets

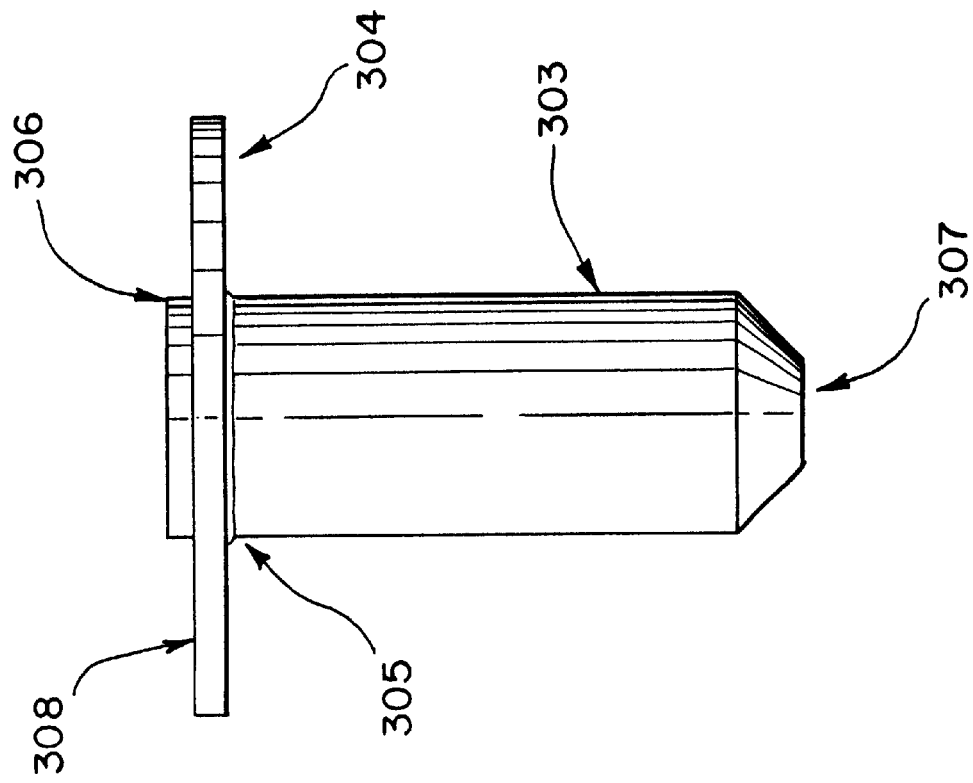
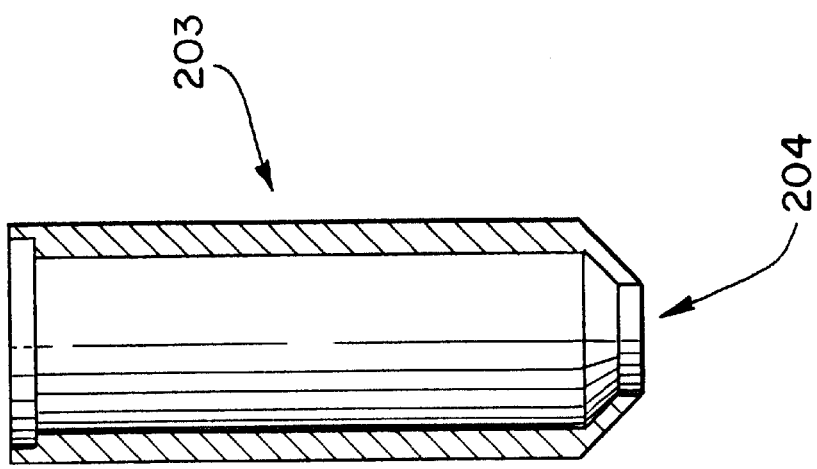

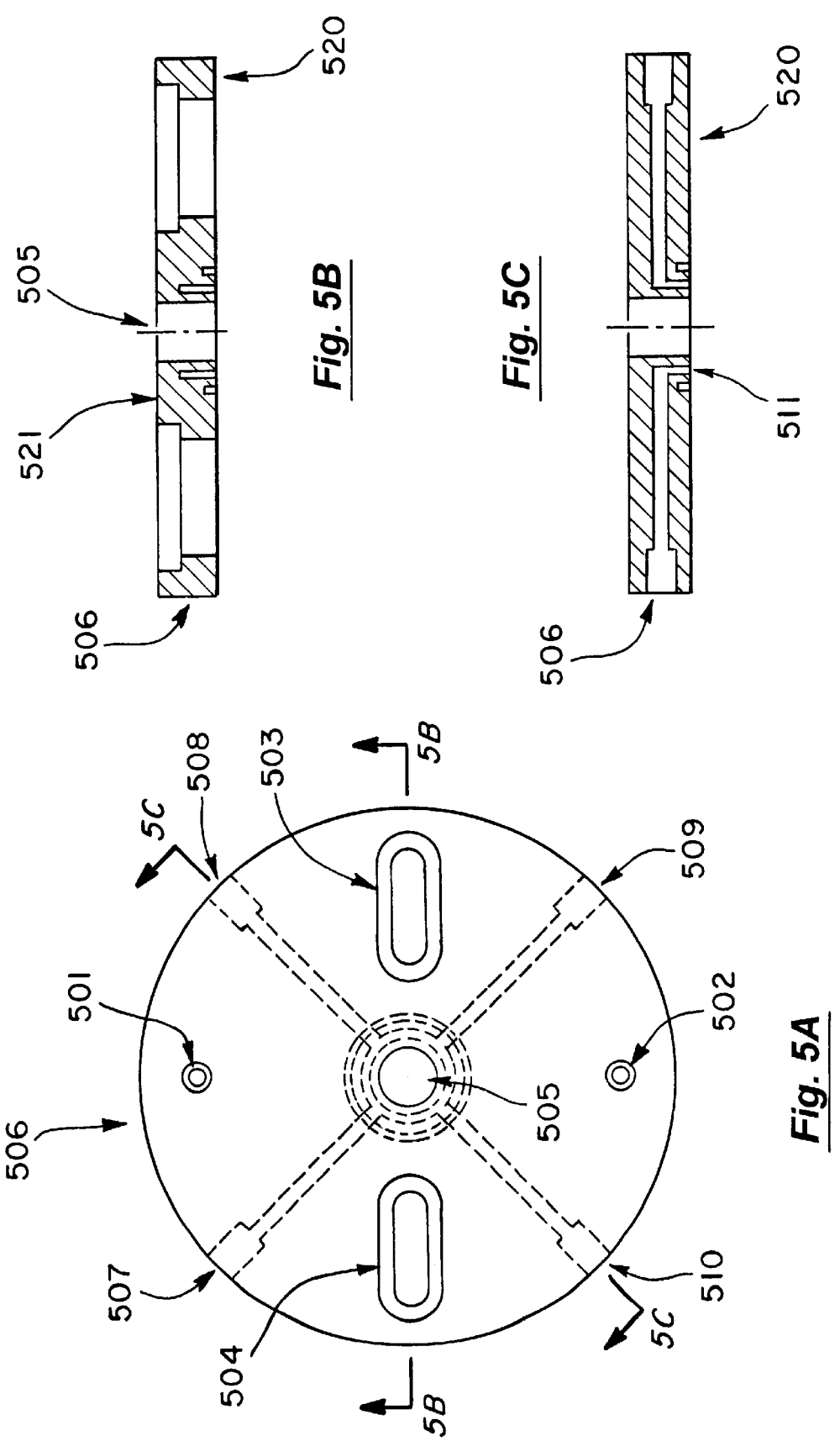

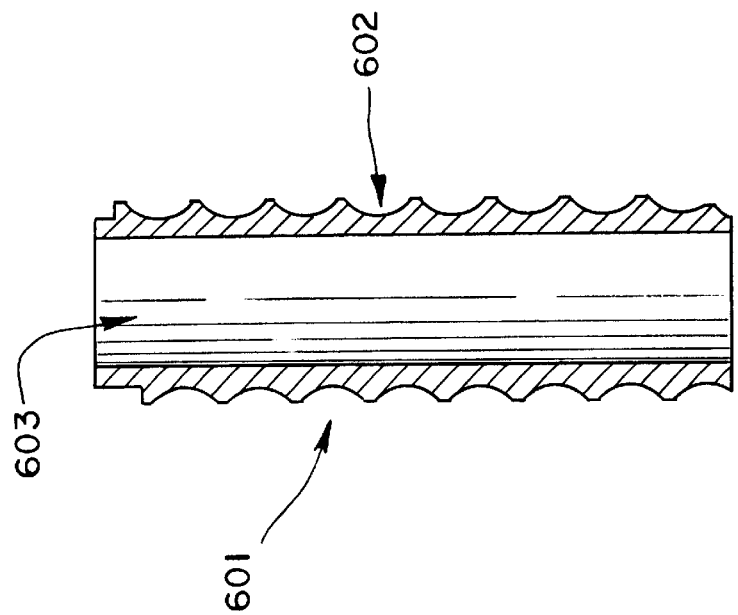
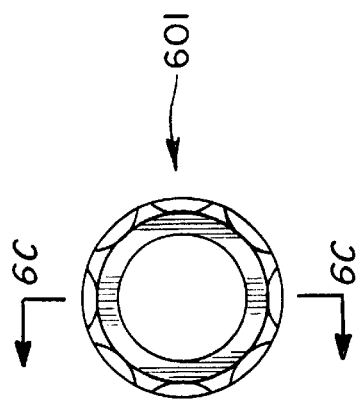
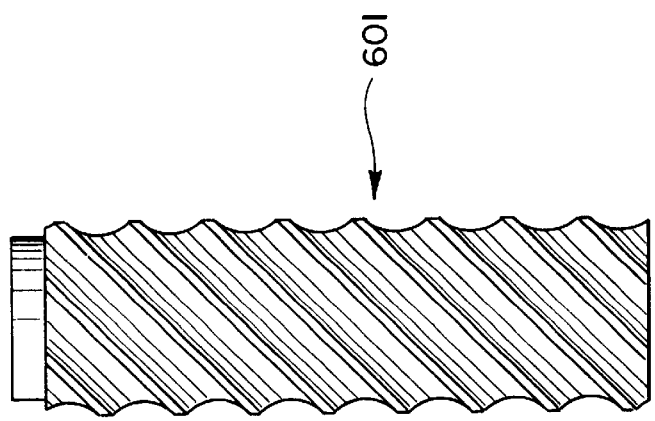

L-10 ADDITIVE STUDY

HIGH TEMPERATURE DIESEL DEPOSIT TESTER

CROSS REFERENCE PATENTS

FIELD OF INVENTION

The present invention relates to a bench top scale device for testing the potential of compression ignition engine fuel compositions which form deposits on engine components during engine operation; and a method for testing said fuel compositions that yields data measuring the propensity of said fuel compositions to form deposits that negatively effect engine operation; said data correlating directly with results obtained in testing said fuel compositions in engines operating under in use conditions.

BACKGROUND OF THE INVENTION

During operation the hot surfaces within an internal combustion engine are exposed to many fluids, both liquid and gaseous, which may undergo thermal breakdown resulting in the formation of deposits on the surfaces of these components, thus compromising engine function. Examples of the fluids which an engine component might be exposed to are fuel compositions, lubricating fluids, and combustion byproducts. Those skilled in the art are aware of the methods and apparatus generally employed for screening fuel compositions for their tendency to form deposits that can compromise engine functionality. Because of the limited ability of bench top scale apparatus and methods to duplicate the conditions encountered in an operating engine, ultimately fuel compositions are tested in a running engine, under simulated "real world" operating conditions to determine how well these fuel compositions perform in terms of suppressing the formation of engine deposits or removing engine deposits once formed. Such tests are expensive, and because of the cost of the equipment and the duration of the test, the use of test engines to determine fuel and other fluid performance is prohibitively costly to do a broadly based "screening" type of study.

Traditionally, bench top scale testing equipment and methods utilized to "screen" fuel compositions for their propensity to form disadvantageous deposits have been based on the notion that simple thermal degradation of fuel compositions can be correlated to the performance of these fuel compositions when they contact "real world" components in "real world" engines operating under "real world" conditions. For this reason, most of the apparatus utilized in such screening tests employ some scheme in which fluids or vapors of the fuel composition are contacted with a substrate and then heated, generally under steady state conditions. However, it is well known in the art that simple static heating of a fuel composition and observation of the amount of deposits thereby formed correlates poorly, if at all, with performance of such fuel compositions in engines operating under real world or simulated real world conditions. Those skilled in the art understand that many factors in addition to thermal conditions within the engine environment influence the formation of engine deposits. These factors include the nature of the fuel composition, the type of material from which an engine part is made and its surface finish, the thermal history of the surface during its exposure to the fuel composition, and the presence of other fluids (such as coolant, engine exhaust, or lubricant vapors) admixed with the fuel composition during contact with the engine part's surface. Additionally construction features of the engine components such as fine passageways, orifices, or sharp edges can also contribute significantly to variations in the rate of deposit formation and its impact on engine functionality.

To illustrate this point, an example from the prior art of fuel testing apparatus may be cited. In U.S. Pat. No. 3,059,467 to Meguerian et. al. an apparatus is described in which a metered continuous flow of liquid fuel is passed along an inclined heated conduit along with a stream of air, the heated region being either of uniform temperature or a gradient temperature over the length of the conduit, and the heating being either steady state or increasing throughout the determination. After a period of time during which fuel and air are passed through the apparatus, the conduit is removed from the apparatus and weighed, the weight being compared to its weight prior to exposure to the fuel composition to determine the amount of deposits left by decomposition of the fuel. The results obtained using this method were compared with results of two different "real world engine" tests. These data showed that for a given fuel composition and set of test conditions repeatability of the apparatus was poor. In several identical tests the apparatus yielded deposit weights wherein the highest recorded was 135% of the lowest recorded.

A series of Chevorlet ISD engine tests were run using different fuel compositions and compared with those same fuel composition run in the subject apparatus. Data derived from the engine tests showed that a fuel that failed the test deposited 334% greater weight of deposits than a fuel that passed the test. Tests conducted on those same two fuel compositions using the subject apparatus and method of Meguerian et. al. gave results wherein the failing fuel composition produced deposits only 149% heavier than those of the passing fuel composition. Comparison of the data obtained from the repeatability tests with those of the data obtained from the passing and failing fuel tests indicates that the testing method of Meguerian may not give a good indication of the propensity of a fuel composition to form deposits in situations where deposit formation is dependent upon factors other than the raw chemical propensity of a fuel composition to thermally decompose. As the deposit formation is increasingly dependent upon factors other than mean operating temperature, testing equipment based upon simple thermal decomposition of fuel compositions correlates less well with the results obtained from the same fuel composition employed in an operating engine test.

Operating conditions also contribute to variations in deposit formation within engines. For example an engine running under constant load will form deposits at a different rate than one which is subjected to cycles of acceleration and deceleration under varying load and coast conditions.

In general, for bench top scale testing equipment to mimic conditions, and thus more accurately gauge the propensity of fuel materials to form deposits which lead to impairment of engine operation, they must incorporate features which permit cycling through various temperature conditions and conditions of fuel composition loading on the surface, as well as the ability to introduce other fluids into the testing apparatus under the conditions in which they would contact a surface in an operating engine. Additionally, testing apparatus must be designed so that channels and other surface features that appear within an engine are mimicked in the testing apparatus. Finally, for any apparatus to test the propensity of a fuel composition to leave deposits within an engine, it must address the problems associated with variations in surface composition and finish of the substrate upon which deposits are left within the testing apparatus, as well as provide a means of reproducibly providing a substrate surface of accurately measured surface area and finish, one of the keys to reproducible test results. Presently, this factor is either largely ignored, or is addressed through the requirement of requiring an expensively custom machined and finished substrate, resulting in elevated costs associated with testing apparatus. Due to the expense of such substrates, practitioners typically resort to cleaning the substrate after use, which preclude preservation of samples and often leaves the quality of the resulting surface finish in doubt from the perspective of a reproducible surface.

Accuracy of devices employing gravimetric measurement of deposits left on a substrate surface also suffers when low surface area substrates are employed from the standpoint that minimal catalytic surface/volume of fuel leads to small amounts of deposits being formed (thus the range of weight change in the substrate for various fuel compositions is small), and the surface area to weight ratio is low, making it difficult to accurately measure the weight change.

Additional factors, such as non-uniform distribution of fuel compositions within the test apparatus, and fuel puddling within the test apparatus can also effect the reproducibility of test data.

Operating conditions are of utmost importance when testing fuel compositions intended to be burned in diesel engines. This is particularly true when concerned with the tendency of diesel fuel compositions to leave deposits within fuel injectors. Unlike spark ignition engines, compression ignition engines have fuel delivery components exposed to combustion chamber temperatures, and during operation under "motoring" conditions (engine operating under coasting or braking conditions), very high temperature gas is forced into the injectors, resulting in degradation of fuel residue left in the injector. For this reason, an apparatus used to examine the tendency of diesel fuel compositions to degrade and leave deposits must permit tests to be conducted at temperatures near the flash point of the fuel composition. This requires testing equipment that is designed to address the safety issues associated with such high temperature testing. Additionally, automating the testing equipment affords the ability to conduct tests in which the conditions within the testing apparatus are cyclic rather than static, giving a testing regime which more nearly matches the environment found in an operating engine.

U.S. Pat. No. 5,693,874 to De La Cruz discloses a test apparatus designed to simulate the conditions of the intake manifold in a gasoline engine employing port fuel injection, and the attendant conditions in which an intake valve in such a gasoline engine operates. The design is unsuitable to testing diesel fuels because of the low surface area to weight ratio of the test specimen and the absence of safety devices that would permit high temperature soak cycles.

U.S. Pat. No. 3,438,248 to Taylor et. al. discloses a device wherein the thermal decomposition of bulk fuel flow over metallic test strips may be examined. Taylor is directed at studying the conditions most commonly found in nearly empty fuel tanks of aircraft traveling at supersonic speeds. This device does not closely approximate the conditions found in an operating diesel engine and does not incorporate safety features necessary to conduct such tests at temperatures which approach the conditions found in an operating diesel engine.

U.S. Pat. No. 3,318,667 to Fabuss et. al. discloses a device designed to duplicate the results of the ASTM-CRC fuel coker test apparatus while using a drastically lower volume of fuel material in the test. Fabuss is directed at studying the thermal decomposition of fuel compositions under conditions of bulk liquid fuel flow such as would be found in the systems supplying fuel to the engines of high performance aircraft. It is not suited to studying decomposition of residue under conditions simulating those in the combustion chamber of an operating diesel engine because it relies on liquid fuel flowing through the apparatus to perform the test. This also precludes testing under conditions in which the test surfaces are exposed to gases and vapors having the chemical characteristics of other fluids such as lubricant or exhaust gas during the test.

U.S. Pat. No. 3,059,467 to Meguerian et. al. discloses an apparatus in which liquid fuel is passed along a heated conduit, the conduit being subjected to gravimetric analysis before and after exposure to the fuel. The conduit has a low surface area to mass ratio which can negatively effect the sensitivity of test data to the propensity of a fuel to form engine deposits. As with other such apparatus used to study the thermal degradation of liquid fuel streams, this device is also unsuited to simulating the conditions to which components in the combustion chamber of a diesel engine are exposed.

The present invention provides a method in which a highly reproducible low cost surface mimicks the structural morphology typically found within engines. Additionally it provides an apparatus in which the operating extremes typically found in operating diesel engines may be duplicated while maintaining a safe working environment. Additionally it provides a method of automatically determining the propensity of diesel fuel materials to form deposits within diesel engines that has good correlation with tests performed in running diesel engines.

SUMMARY OF THE INVENTION

One aspect of the present invention is to provide a bench scale apparatus in which diesel fuel compositions may be examined for their propensity to leave deposits in diesel engines under operating conditions.

Another aspect of the present invention is to provide a method of using the apparatus to test the propensity of diesel fuels to leave deposits in operating diesel engines.

Another aspect of the present invention is to provide a method of utilizing low cost materials in the testing apparatus that give a highly reproducible substrate upon which deposits are formed during the test.

Another aspect of the present invention is to provide a bench top scale apparatus in which diesel fuel compositions may be safely tested at the extreme operating conditions typically experienced in an operating diesel engine.

Yet another aspect of the present invention is to provide an apparatus in which testing of diesel fuel compositions is completely automated, requiring technician input only to set up the testing conditions and retrieve the substrate at the end of the test period.

An additional aspect of the present invention is to provide a method of utilizing a low cost substrate that leads to improvement in the sensitivity of gravimetric measurement of deposits formed during tests carried out to determine the propensity of a diesel fuel composition to leave deposits in a running engine, accomplished by increasing the surface area to mass ratio of the substrate employed over that conventionally used in fuel testing apparatus.

A further aspect of the present invention is to provide an apparatus in which the parameters of fuel loading and thermal excursion may be adjusted dynamically over a broad range, permitting testing to be carried out under conditions which closely mimic those experienced in an operating diesel engine.

Yet another aspect of the present invention is to provide an apparatus in which the conditions experienced within an operating diesel engine are further mimicked through the ability to entrain vapors and gasses that mimic other fluids such as lubricating oil and coolant encountered in an operating diesel engine.

An additional aspect of the present invention is to incorporate fire suppression equipment and a method of automatically actuating the fire suppression equipment during a determination carried out in the testing apparatus.

Another aspect of the present invention is to provide an apparatus and a method of using the apparatus to study the propensity of diesel fuel compositions to leave deposits deleterious to the operation of diesel engines which has a high degree of correlation between test data derived from the apparatus and the results observed in operating diesel engines.

Other aspects of this invention will appear from the following description and appended claims, reference being made to the accompanying drawings forming a part of this specification wherein like reference characters designate corresponding parts in several views.

BRIEF DESCRIPTION OF THE DRAWINGS

Before explaining the disclosed embodiment of the present invention in detail, it is to be understood that the invention is not limited in its application to the details of the particular arrangement shown, since the invention is capable of other embodiments. Also, the terminology used herein is for the purpose of description and not of limitation.

FIG. 2 is a cross sectional representation of the structure of the best mode testing chamber indicated as block element 103 in FIG. 1.

FIG. 3 is a side view of the best mode embodiment testing chamber of FIG. 2 with preferred flange seal half installed.

FIG. 5a is a cutaway top plan view showing machining detail of the best mode conduit plate, represented schematically in FIG. 4 as element 405.

FIG. 5b is a side plan sectional view along axis 5B of FIG. 5a.

FIG. 5c is a side plan sectional view along axis 5C of FIG. 5a.

FIG. 6a is a spiral substrate member, an alternative substrate embodiment.

FIG. 6b is a top plan view of FIG. 6a.

FIG. 6c is a side plan view sectional view along axis 6C of FIG. 6b.

FIG. 7b is a top plan view of FIG. 7a.

DESCRIPTION OF THE PREFERRED EMBODIMENT

Figure 1:
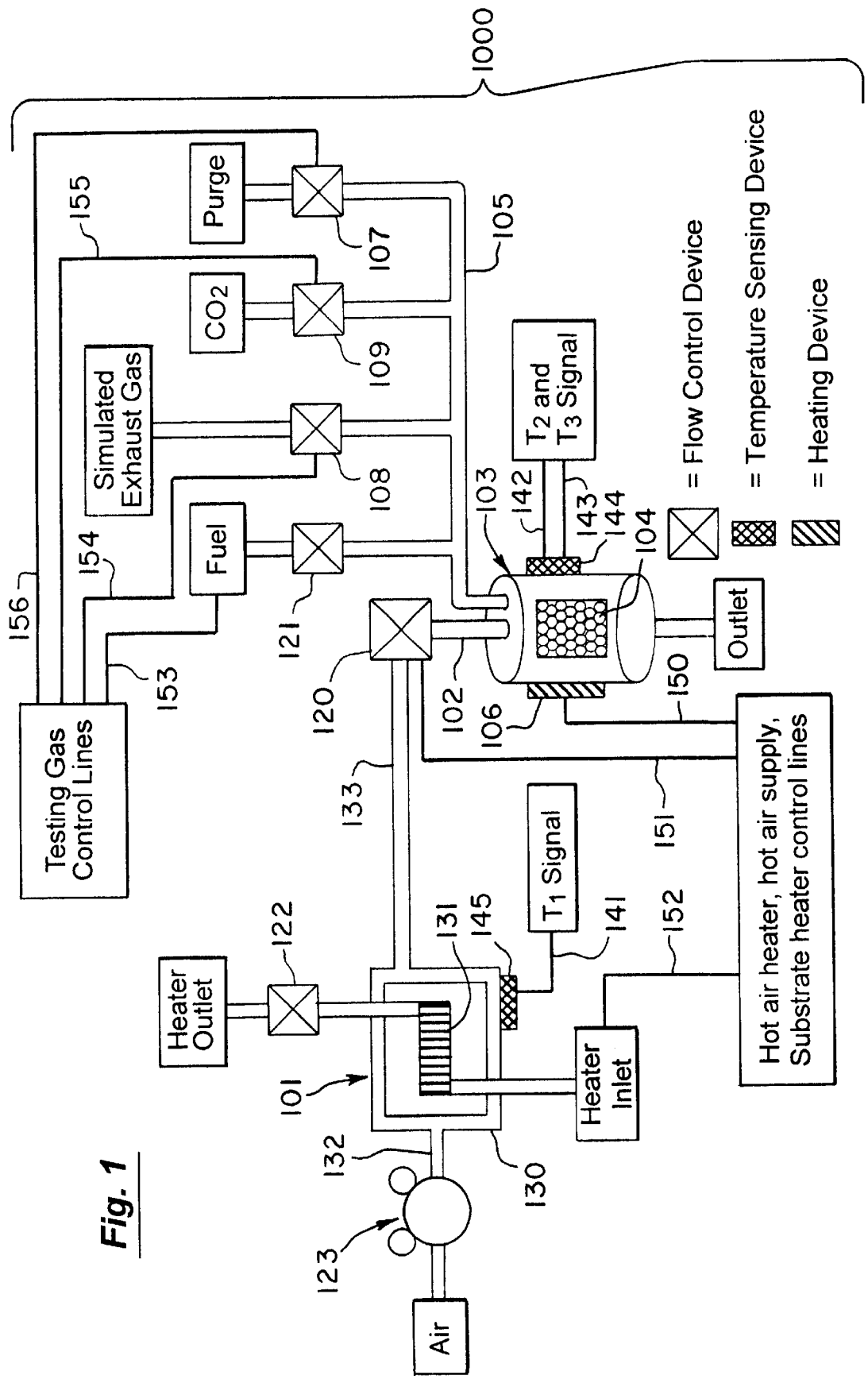
FIG. 1 is a schematic block diagram of the arrangement and connectivity of the elements of the testing apparatus and the control and sensor lines utilized by the automatic control device in the preferred embodiment.

The general scheme of the experimental apparatus may be seen as system 1000 in FIG. 1. With reference to FIG. 1, the system 1000 consists of chamber 101 in which air is heated. Chamber 101 is connected via conduits 133 and 102 to testing chamber 103, which in use contains substrate 104 upon which fuel deposits are formed. Conduit 105 provides a means of conducting various fluids into testing chamber 103, in particular fuel compositions delivered by fuel flow controller 121, and a variety of gas from flow controller 107, 108, and 109. Fuel flow controller 121 also meters fuel onto substrate 104 during testing Testing chamber 103 is in thermal communication with heater 106, which is used for heating the testing chamber surfaces and the substrate therein.

Flow controller devices 107, 108 and 109 may be employed to control the conduct of inert gas, fluid simulating fluids found in the engine environment other than fuel, and/or fire suppressing gas into chamber 103 via conduit 105 during testing. Inert gas or fire suppressing gas passed into testing chamber 103 during a high temperature thermal excursion within chamber 103 in the course of testing a fuel composition or in the event of a fire or explosion occurring within chamber 103 during testing forms an inert gas blanket which acts to suppress fire and explosions.

One skilled in the art will appreciate that there are numerous types of valves and fluid flow control devices which may be employed to control the fluids passing into and out of chambers 101 and 103. For control of air and other gases passing into chamber 103, examples of suitable control devices which are familiar in the art include, but are not limited to, ball valves, diaphragm valves, needle valves, gate valves, and bellows valves, rotometer type volume flow meters, and mass flow controllers. It is contemplated that different embodiments could employ each device alone or in a combination with other devices such that one device is used to control volume or mass flow and another is used to provide positive shut off or redirect flow. Thus, with reference to FIG. 1, flow control devices 120, 122 and 123 may be a simple shut off valve such as a diaphragm valve, a combination of a fixed orifice and a shut off valve, a variable orifice valve such as a needle valve, alone or in combination with a shut off valve, and the various valves may be manually or automatically actuated. In an alternate embodiment, flow control device 120 may be a proportioning type apparatus such as are well known in the art that divide the inlet flow between two outlet legs, one of which is an exhaust or recycle leg, the other being connected to inlet conduit 102 and thence into testing chamber 103.

In the preferred embodiment valves employed in flow control are electrically actuated. An alternate embodiment employs pneumatically actuated valves and an electropneumatic control device to actuate the valves upon receiving an electric signal, such as is well known in the art. In various embodiments it may also be advantageous to insure that fluid is delivered at constant pressure to flow control devices by first passing the fluid being controlled through a pressure regulating device such as a gas regulator and its equivalents such as are well known in the industry.

Fuel flow stop valve 121 is used to introduce a measured quantity of the fuel composition being tested into test chamber 103 via conduit 105. Any arrangement of devices as would be familiar to one skilled in the art wherein an electrically or pneumatically actuated valve is coupled to an orifice (fixed or adjustable) and a fuel supply (either pressurized or gravity fed) may be employed. Examples of valves that may be suitably employed to this purpose are (but are not limited to) a commercially available fuel injector of either a piston pump or pintle valve type construction, pneumatically or electrically operated valves coupled to an orifice (either fixed or variable and a metering pump coupled to a control device which permits it to operate for any number of operator selected strokes in a given cycle. Any arrangement of valves, flow control devices, and pressure regulating devices that can deliver a constant volume of fuel such that it is distributed evenly over substrate 104 as long as the delivery device is actuated is contemplated as suitable for supplying measured quantities of fuel to testing chamber 103. Such devices and control schemes are well known in the art of delivering controlled quantities of fluids.

The preferred embodiment of the fuel metering device in the present invention utilizes a gas pressurized fuel reservoir and an electrically actuated valve controlling flow to an orifice to introduce measured amounts of fuel into chamber 103. Variation in the amount of fuel introduced is operator adjustable on the basis of varying the length of time during which the valve is actuated. Such an embodiment is disclosed in U.S. Pat. No. 5,693,874 to De La Cruz et. al., which is incorporated by reference herein.

In the preferred embodiment, flow of fuel, air, exhaust gas, and inert gas is accomplished by regulating the pressure of the supply and the size of the orifice through which the fluid passes, and the "on time" of a valve controlling passage through the appropriate conduit. Thus, a measured amount of fuel is delivered to the test chamber by supplying an appropriate signal to hold open fuel flow stop device 121 for a period of time that corresponds to the desired quantity of fuel. Flow stop devices 107, 108, and 109 are similarly operated. Alternative embodiments are possible wherein the volume of the fluid is regulated by a mass flow controller or the like, eliminating a requirement for the operator to predetermine delivery rates or make orifice adjustment in the apparatus prior to conducting a test.

With further reference to FIG. 1, in one embodiment chamber 101 consists of outer shroud 130 which is connected to inlet conduit 132 and outlet conduit 133 and encloses heating element 131. Heating element 131 may be of hollow tube construction through which a heated fluid is passed, such as steam or hot oil, or may be an electrical heating element, either device being well know in the art. Together shroud 130 and heating element 131 comprise a heat exchanger, and may be of any convenient configuration to provide heat transfer between the heating element and the air passed into it through inlet conduit 132, such heat exchangers being well known in the art. The source of the air supplied to inlet conduit 132 may be derived from a compressed gas cylinder or supplied by compressor or blower using techniques which are well known in the art. The preferred embodiment of chamber 101 is disclosed in U.S. Pat. No. 5,693,874 to De La Cruz et. al., and is incorporated by reference herein. The De La Cruz patent 874 discloses a hot air supply element in which a pressure regulated stream of compressed gas is passed into a conventional tube within tube heat exchanger, such heat exchanger being well known in the art, the outlet conduit of the heat exchanger being equipped with a relief valve and the heat exchanger working fluid being set to give the desired temperature to the air stream passing thorough it. The disclosed hot air supply system is adapted to use in the present invention by interposing a pressure regulator and flow control device 120 between chamber 101 and testing chamber 103 to permit automatic control of air flow from chamber 101 into testing chamber 103. In the preferred embodiment, flow control device 120 is a pressure regulator coupled to a manually variable orifice and an electrically actuated valve disposed in such a manner that actuating the valve open commences hot air flow, and maintains air flow until the valve is actuated to the closed position. Other embodiments are possible in which the manually variable orifice may be replaced with an electrically or pneumatically variable orifice such as are well known in the industry, or with a proportioning throttle type valve which would provide a constant flow of gas through the heat exchanger, giving a constant temperature but permitting hot air volume passing through chamber 103 to be varied. An additional embodiment is contemplated in which highly accurate swings in air temperature may be produced in which a proportioning valve is employed to mix streams of hotter and colder air to produce an air stream of the desired temperature. Using such a device would permit rapid and highly accurately controlled thermal excursions to be directed to test chamber 103 that ranged from the temperature of the cooler air stream to that of the hotter air stream. In the preferred embodiment of the hot air supply, temperature excursions are accomplished by raising the temperature of the heat exchanger working fluid or reducing the flow rate through the heat exchanger or a combination of the two.

With reference to FIG. 1, chamber 103 may be of any convenient shape or configuration that permits good thermal contact between the walls of testing chamber 103, heating device 106, and substrate 104 placed within test chamber 103. It may be that different forms of substrate 104 may find one particular shape more advantageous than another for testing chamber 103.

Testing chamber 103 may be insulated or uninsulated, and it may be internally or externally heated by such devices as are well known in the art. Examples of suitable heating devices are (but are not limited to) fluid heat exchangers and electrically powered resistance heating elements. The important design elements of testing chamber 103 is that it provide a flow through design, and provide that fluids introduced into testing chamber 103 are dispersed so as to contact the surfaces of substrate 104 placed within the chamber uniformly. Additionally, testing chamber 103 should afford a tight, thermally robust seal so as to insure containment of fuel compositions and air/fuel mixtures evolved during testing. A final design requirement for testing chamber 103 is that it have an access way of sufficient dimension to permit placement and withdrawal of the substrate without disturbing any deposit layer which may have been left on the surface of the substrate in the course of a test.

One embodiment of the schematic element testing chamber 103 is shown with reference to FIG. 2, as cylindrical testing chamber 203. Cylindrical testing chamber with a conical shape imparted to its outlet end 204 is the preferred form of the testing chamber of the present invention. The conical shape of the outlet is of particular advantage in suppressing the formation of fuel droplets and fuel puddles within the chamber. The presence of droplets and puddles of fuel has been found to negatively influence repeatability in sequential determinations conducted under the same testing conditions in bench top scale fuel testing apparatus.

The best mode of attaching testing chamber 203 into an assembled testing apparatus is shown with reference to FIG. 3, flange mounted testing chamber 303 (wherein the cylindrical section testing chamber and conical outlet 307 of testing chamber 303 is equivalent to testing chamber 203 of FIG. 2). Testing chamber 303 is a hollow cylinder in form, with a flange plate affixed at the inlet end and a conical internal profile at the other. In the best mode, the flange half affixed to the inlet end of the testing chamber (face 306) mates with a similar flange face machined into, with reference to FIG. 5c, face 520 of conduit plate 506, and by any flange sealing means as are well known in the art, the testing chamber is affixed to the rest of the testing apparatus.

The cylindrical form of the testing chamber provides the advantage that it is an easy and cost effective shape to machine, and the cylindrical walls provide a convenient shape for the external attachment of cylindrical sections of heating elements, the testing chamber outer diameter being sized to give close contact between the chamber walls and cylindrical section electric heating element sections, such elements being well known in the art.

Figure 4:
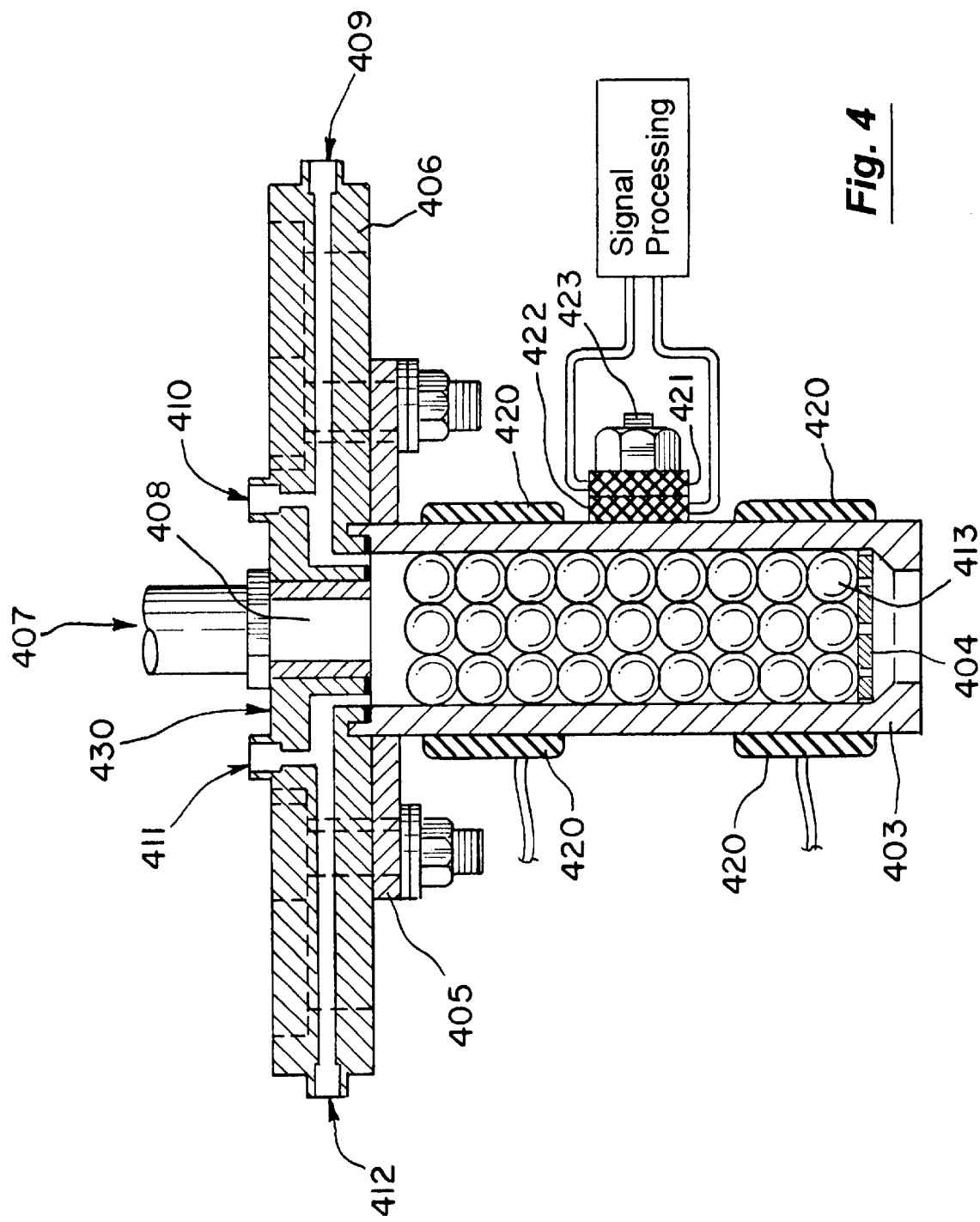
FIG. 4 is a cross sectional schematic diagram of the FIG. 3 flange sealed testing chamber assembled to a conduit plate and containing ball bearing substrate.

A schematic of the testing chamber charged with substrate is shown in FIG. 4. Of particular note in the assembled testing chamber is the location of two cylindrical section electric heaters 420 placed about the external diameter of testing chamber 403, one near the inlet and the other near the outlet. Alternatively, testing chamber 403 could have affixed to it heat exchange conduit through which a fluid is passed to heat the chamber. Additional alternative embodiments are possible in which well insulated electrically powered heating elements or conduits through which a heat exchange fluid is passed may be placed within the chamber, or testing chamber 403 could even be of hollow wall construction with a heat transfer fluid passed through it, such as is well know in the processing arts.

With further reference to FIG. 3, the best mode of the present invention is for one end of cylindrical test chamber 303 to be supported by one half of a conventional flange closure, either welded or of rotatable construction such as is well known in the art. In the best mode, test chamber 303 is welded to flange half 304 at location 305. A sealing lip may be located on sealing face 308 of flange half 304, but in the best mode, the end of cylindrical testing chamber protruding from the flange is provided with sealing lip 306 is located on the open end of testing chamber 303. When assembled with other parts disclosed below, sealing lip 306 forms a seal suitably robust to withstand the testing conditions. Conical bottom 307 of chamber 303 has a hole bored through it and is fitted with an outlet conduit to conduct fluids from the test chamber. Many fittings are suitable and are well known in the art, but may include compression fittings, threaded fittings, small flange fittings and the like.

With reference to FIG. 4, testing chamber 403, which is the equivalent to FIG. 1 testing chamber 103, is shown sealed with a flange type sealing device. Testing chamber 403 is joined to lower flange half 405 which in turn is bolted to conduit plate 406 to effect a sealed testing chamber. With reference to FIGS. 5a, 5b, and 5c, conduit plate 506, which is the same as FIG. 4 conduit plate 406, is machined of any metal capable of withstanding the conditions of the testing chamber. In the best mode plate 506 is made of mild steel, but one practiced in the art will readily understand that it may be made of stainless steel, aluminum, brass, copper, monel, titanium, and the like. Plate 506 is through bored across its thickness to form flange mounting bolt holes 501 and 502, and flange mounting oblong bolt holes 503 and 504. Additionally, centered in conduit plate 506 is air stream conduit inlet hole 505, also bored through the thickness of conduit plate 506. Further, with reference to FIG. 5b, face 520 of conduit plate 506 is adapted to mate, with reference to FIG. 3, to sealing surface 306 of the testing chamber. Face 521 of conduit plate 506 is machined to mate, with reference to FIG. 4, to air stream inlet conduit 407. One skilled in the art can appreciate that numerous coupling schemes are well known, such as a flange with a knife edge sealing surface and ductile metal gasket, machined flange faces sealed with fiber gasket packing, internally or externally threaded passage way and sealant, compression fitting and the like.

With reference to FIG. 4, the preferred method of attaching the testing chamber to the testing apparatus and sealing the testing chamber is with a flange and metal gasket mating surface between test chamber 403 and the lower face of conduit plate 406, with heated air stream conduit 407 welded to the upper face of conduit plate 406 in such a manner that it is coaxial with through bored hole 408, hole 408 being identical with FIG. 5a through bored hole 505.

With reference to FIGS. 5a, 5b, and 5c, conduit plate 506 additionally contains four lateral passageways, 507, 508, 509, and 510. These passageways are blind bored laterally parallel with the plate faces, starting at the edge of conduit plate 506 and terminating before they encroach on through bore passageway 505. They are spaced equidistant about the perimeter of the plate and normal to the plate edge. As is shown in FIG. 5b, four blind holes exemplified by hole 511 are bored through the test chamber mounting face 520 of conduit plate 506 such that a right angle conduit is defined, one for each lateral passageway. Grooves, concentric with through bored hole 505 and machined into face 520 could be used instead of blind holes such as 511 for each passageway.

With reference to FIG. 4, other embodiments of the assembly defined by the junction of testing chamber 403, conduit plate 406, and heated air inlet conduit 407 are possible. Both testing chamber 403 and heated air stream conduit 407 could be fixed to flange plates which mate to a double sided conduit plate 406 by flange and gasket coupling arrangement, such as is well known in the art. Alternatively, conduit passageways 409,410,411, and 412 which pass through conduit plate 406 could be effected by boring blind holes 411 and 410 through face 430 of conduit plate 406 to intersect the lateral blind passageways, thus effecting the same number of conduit inlets to the testing chamber but requiring fewer lateral blind passageways to be machined into conduit plate 406.

Finally, with reference to FIG. 5a, in an alternative embodiment, lateral passageways 507, 508, 509, and 510 may be through bored to intersect hot air stream conduit 505, requiring no blind holes exemplified by blind hole 511 to effect passageway into the testing chamber.

It will be appreciated by one skilled in the art that there are many other arrangements of passageways, holes, and fastenings which could be used to effect a testing chamber that could be sealed and have gas inlets and outlets which are well known in the art and would equally serve the purpose of containing a substrate in a controlled atmosphere.

Other embodiments are possible in which any number of conduits are affixed directly to conduit plate 406 and/or testing chamber 403 and/or heated air stream conduit 407.

With further reference to FIG. 4, testing chamber is shown to contain substrate 413 retained at the bottom of said chamber with a perforated or mesh plate 404. In the best mode of the present invention, testing chamber 403 is a hollow cylinder having a conical tapering outlet end which is fitted at the conical end with a plate containing through punched holes of a size sufficient to permit fluids to pass from testing chamber 403 and retain packing material 413 within testing chamber 403 under conditions of full volume flow of test fluids.

With further reference to FIG. 4, substrate 413 may be made in any convenient shape and in any material which mimics the catalytic surface of metals found in the engine environment. The best mode substrate material is grade 25 ¼" hardened stainless steel ball bearings. It will be apparent to one familiar with the art that any ball bearing with a surface finish of grade 25 or better may be employed. The use of ball bearings offers several advantages over other substrates in that they are inexpensive, have very consistent surface finish bearing to bearing, yielding a substrate surface that is highly reproducible from test to test and ball bearings have a large surface area to mass ratio improving the sensitivity of gravimetric measurement of the amount of deposits formed.

It will be appreciated by one skilled in the art that the packing arrangement of the ball bearings comprising the substrate may be altered by varying the diameter of cylindrical chamber 403 such that successive layers of substrate may be placed exactly on top of each other or associated in varying degrees of interstitial arrangement, such as is well known to those in the art of packing arrangements of regular solids. Using these well known packing principles varying size voids may be created within chamber 403 which may be used to model different sizes of fine passageways in internal combustion engines. It will be appreciated by one skilled in the art that similar results in creating different sizes of passageways may be achieved using varying mixtures of spherical substrate having 2 or more different diameters within a chamber of a given size.

A further feature which will be apparent by referring to FIG. 4 is the placement of temperature sensing devices 421 and 422, which in the best mode is thermally coupled to the exterior wall of cylindrical chamber 403 via stud 423 welded to the exterior side wall of testing chamber 403, although alternate equally suitable mounting arrangements are well known in the art. In the preferred embodiment the temperature sensing elements are thermocouples. Thermocouple 421 is employed to monitor the temperature of the packing material while thermocouple 422 is employed to sense an over temperature condition within chamber 403 during a test. It will be appreciated by one skilled in the art that any arrangement of temperature sensing devices which maintains thermal contact with substrate material 413 may be used. By way of example, but not intended to be limiting, in a different embodiment, a temperature sensing device resides within chamber 403 in direct thermal contact with the substrate, electrical contact being provided by feed through electrodes inserted in conduit plate 406, such feed through devices being well known in the art.

Temperature sensing devices are also not limited to thermocouples, but any device suitable to the temperature range of the test may be employed, such as devices based upon a resistance element or upon fluid expansion, such devices being well known in the art.

Although the preferred embodiment of the present invention utilizes ball bearings as a substrate within the testing chamber, as detailed above, an alternative embodiment of the substrate may be understood by reference to FIGS. 6a, 6b, and 6c wherein the spherical ball substrate is replaced with a hollow cylindrical substrate 601 which has had the exterior surface cut in a plurality of spiral grooves 602, and which is dimensioned such that it fits snuggly, with reference to FIG. 4, within testing chamber 403. When such a substrate is employed, cylindrical section heaters 420 are not employed and support plate 404 is not required.

With reference to FIG. 6c, a further feature of substrate 601 is that it is axially through bored such that it has a hollow center, 603, which is dimensioned such that it snuggly accommodates an electrical cartridge style heater, such heaters being well known in the art.

Figure 7B:
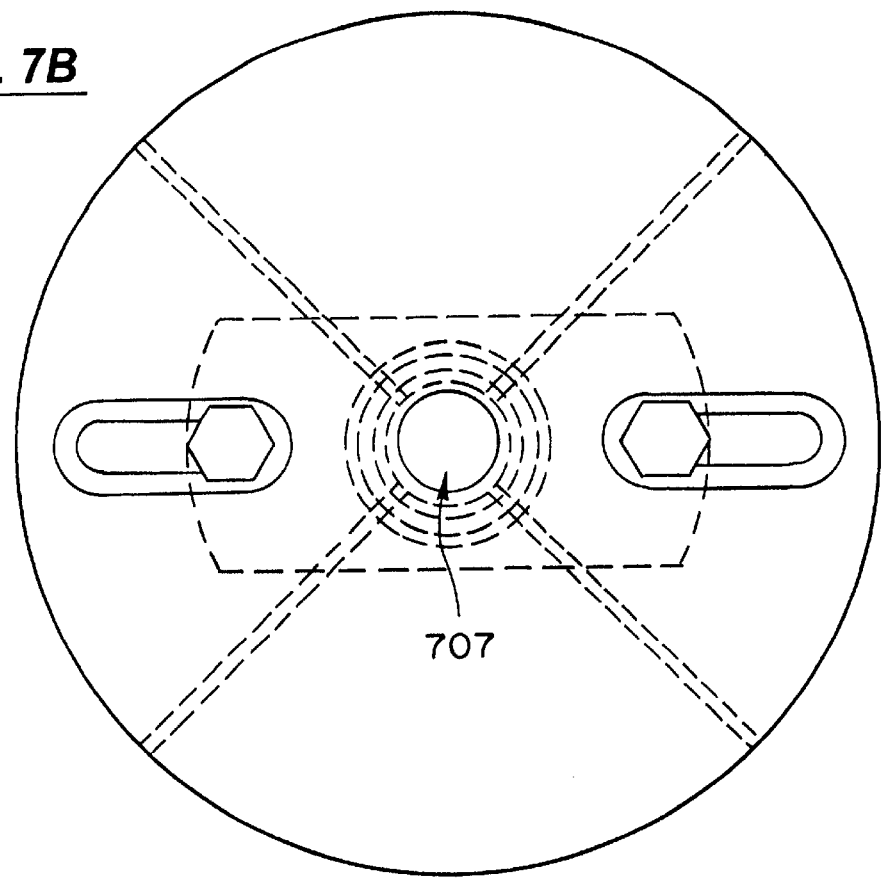
Figure 7A:
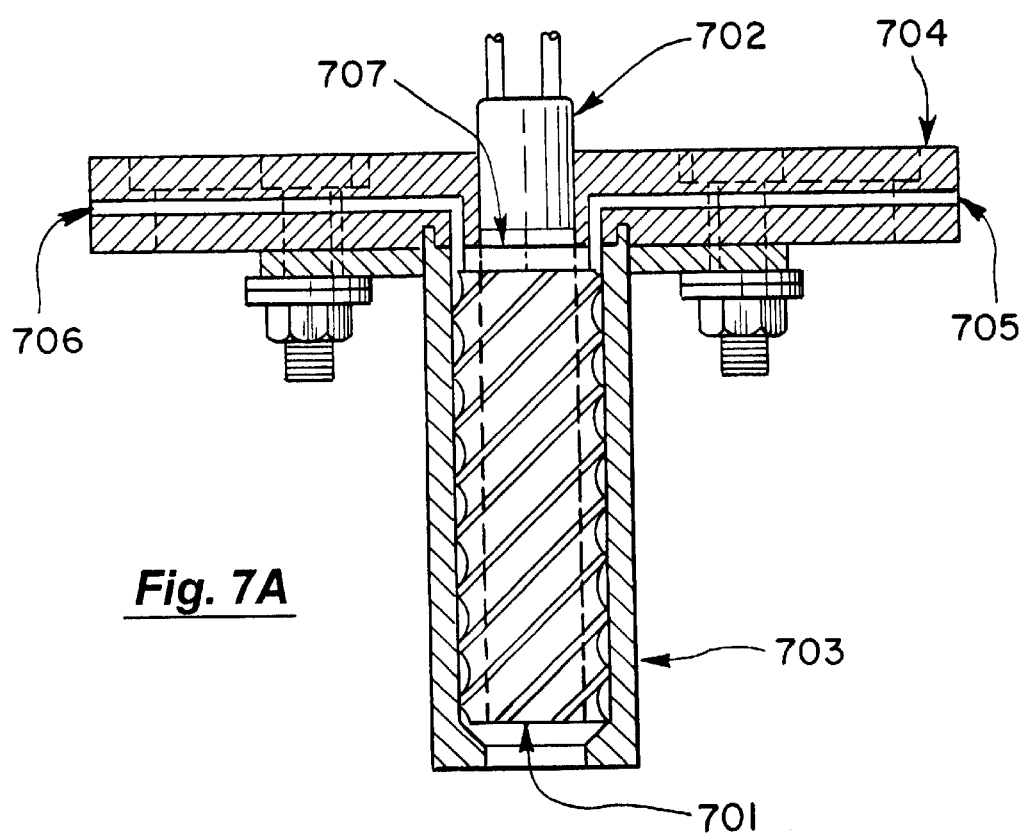
FIG. 7a is a cutaway view of an alternative embodiment testing chamber with spiral substrate member therewithin.

With reference to FIG. 7a, the spiral type packing 701, which is the equivalent of spiral packing 601 of FIGS. 6a, 6b, and 6c, is inserted into test chamber 703 (dimensioned so that the external fins of spiral packing 701 fit snuggly against the interior walls of testing chamber 703, testing chamber 703 being the equivalent of chamber 403 of FIG. 4. It will be appreciated by examining FIG. 7a that fluid passed into the top of testing chamber 703 will be forced along the spiral grooves of spiral packing 701. It will further be appreciated that because it is hollow to accommodate a cartridge heater the ratio of spiral packing 701 surface area to it's weight is greater than that of a similarly sized solid machined piece, thereby improving the accuracy of gravimetric measurement of deposits left on the surface of spiral packing 701 over similar deposits left on solid shapes of similar design.

It will be appreciated from inspection of FIG. 7a that when spiral substrate 701 is employed instead of ball bearings, cartridge heater 702 passes through, with reference to FIG. 5, through bored hole 505 in the center of conduit plate 506. Conduit plate 704 is identical to conduit plate 506 of FIG. 5, and has the same bored through holes and passage ways as conduit plate 506. With reference to FIG. 7a, when spiral substrate 701 is used the heated air stream conducted into the testing chamber through one of the radial passageways (exemplified by passageways 706 and 705) bored into conduit plate 701 instead of through central hole 707 as was described for a ball bearing substrate embodiment.

It will be appreciated by one skilled in the art that many other forms of substrate may be employed in a suitably designed chamber, such as random shapes, sands, nodules, and coils of material having similar composition and surface finish to the engine components which they model. The only requirements is that they pack in such a manner that passageways are uniformly distributed through the substrate mass, and that they are in sufficient thermal communication with each other and the walls of the test chamber in which they reside that their temperature may be adequately monitored and controlled via the testing chamber heating system and temperature sensing devices associated with the testing chamber as described in detail above.

In the preferred embodiment of the present invention the testing apparatus, and therefore the conduct of a test, is controlled automatically by electrically actuated flow control and temperature control devices driven by a computer or industrial controller/timer such as are well known in the art. FIG. 1 indicates which devices are controlled and which are monitored by indicating control or monitor line connection to the various schematic elements. Thus, with reference to FIG. 1, the monitoring lines are shown as heated air heat exchanger temperature monitoring line 141, substrate temperature monitoring line 142, and over temperature monitoring line 143. Temperature sensing devices 144 and 145 may be thermocouples as discussed hereinabove in connection with FIG. 4, thermocouples 421 and 422. Control lines shown in FIG. 1 are testing gas control lines 153, 154, 155, and 156; heated air flow control line 151, substrate heater control line 150, and air heater control line 152. The temperature monitoring lines are connected to an automatic controller which receives information from the associated temperature sensitive element, such as are well known in the art, and, using the associated device control line (also connected to the automatic controller) alters the power supplied to the related device to adjust the output according to an operator selected set point. Thus, sensor line 141 transmits signals proportional to the temperature of the air stream passing out of the chamber 101 and the controller adjusts the temperature of the air stream passing out of chamber 101 according to an operator selected set point via control line 152. In like manner, temperature sensor line 142 sends a signal to the controller proportional to the temperature of the substrate within testing chamber 103 and adjusts power accordingly to heater 106 via control line 150. In the same fashion, temperature sensor line 143 also sends a signal proportional to the temperature of the substrate within testing chamber 103 and if an operator selected maximum is exceeded the controller shuts off power to heater 106, discontinues fuel dosing by interrupting power to fuel flow controller 121 via control line 153, and actuates the fire suppression system, opening flow control device 109 via control line 155.

Furthermore, in the preferred embodiment, in addition to controlling the heaters and flow control devices which vary testing conditions, the controller employed has the capacity to control the timing of fuel dosing/soaking and hot air bake cycle automatically, according to values set by the operator prior to running a determination. Additionally, in the preferred embodiment, the controller contains a testing cycle clock to control the duration of the test, such duration being adjustable by the operator.

Figure 10:
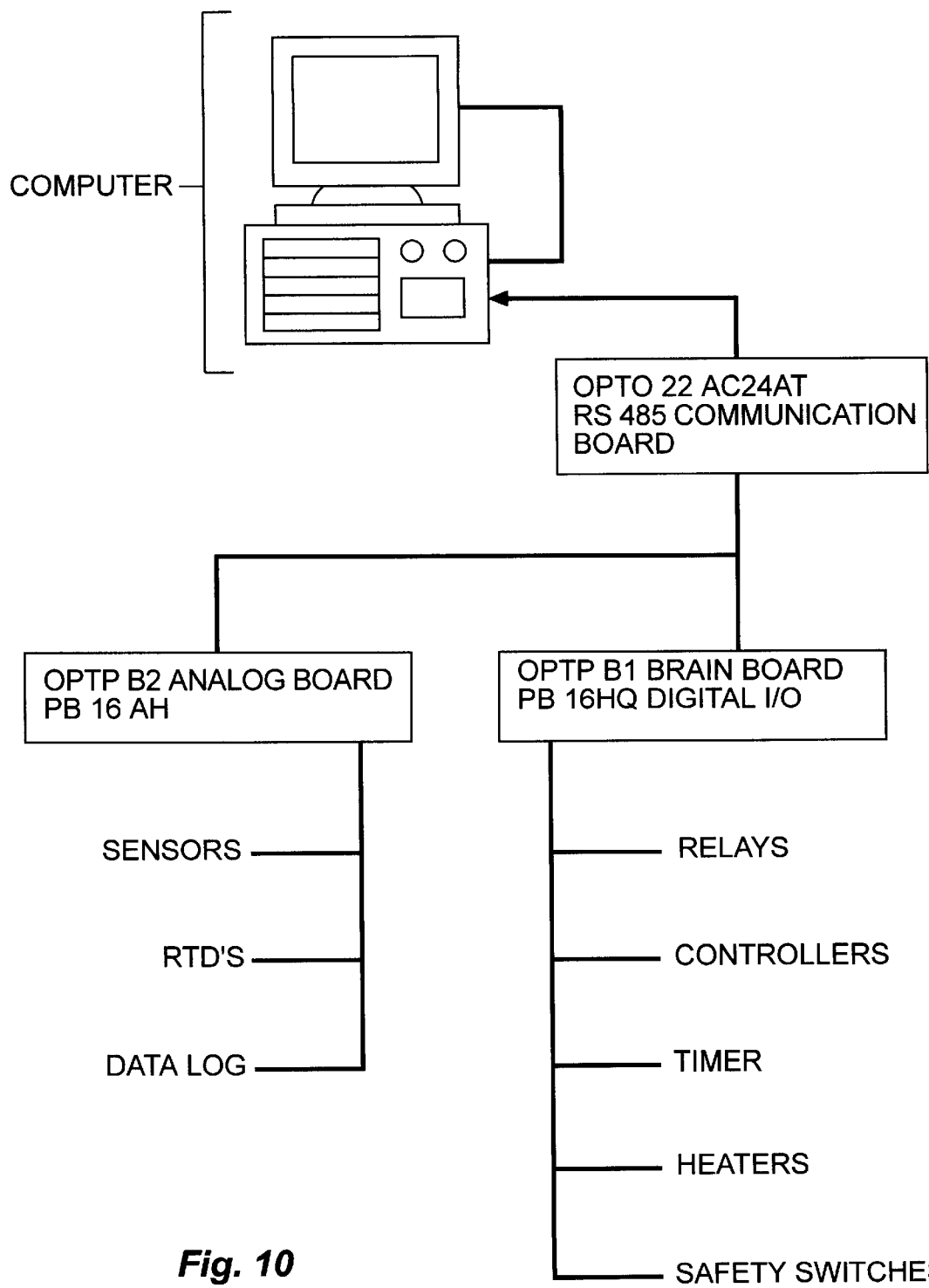
FIG. 10 is a schematic illustrating integration of the electrical control and sensor signals for employing a digital computer to control the testing apparatus.

With Reference to FIG. 10, the best mode contemplated for control and timing of operations such as the opening and closing of valves and control of temperature and flow control in the various devices employed in the subject apparatus is contemplated to be by digital computer fitted with the appropriate interface boards, such as will be familiar to one skilled in the art. By way of example, although not limited to be limiting, a Pentium Corporation OptomuxR System may be fitted to any digital computer of the PC designation to effect the required control of the appratus. It will be apparent to one skilled in the art that any of the numerous other systems designed to collect analog signals and convert them into a format compatible with a digital computer, and to receive digital signals from a digital computer and convert them into signals suitable for actuating control devices may also be employed. It will also be apparent to one skilled in the art that, even though more difficult to implement, control may be achieved by using one or more stand alone programmable controllers such as is exemplified by a Square D products Class 8005 Model 50 Programmable Controller.

In the preferred embodiment, all controllers controlling heating devices are capable of effecting the typical control schemes such as are well known in the art, examples of which are (but not limited to) simple analog response, proportional response, and pulsed signal response to an input signal condition calling for adjustment of the conditions in the testing chamber. Other embodiments are contemplated in which controllers having only simple analog or closed loop control capabilities are employed.

Figure 8:
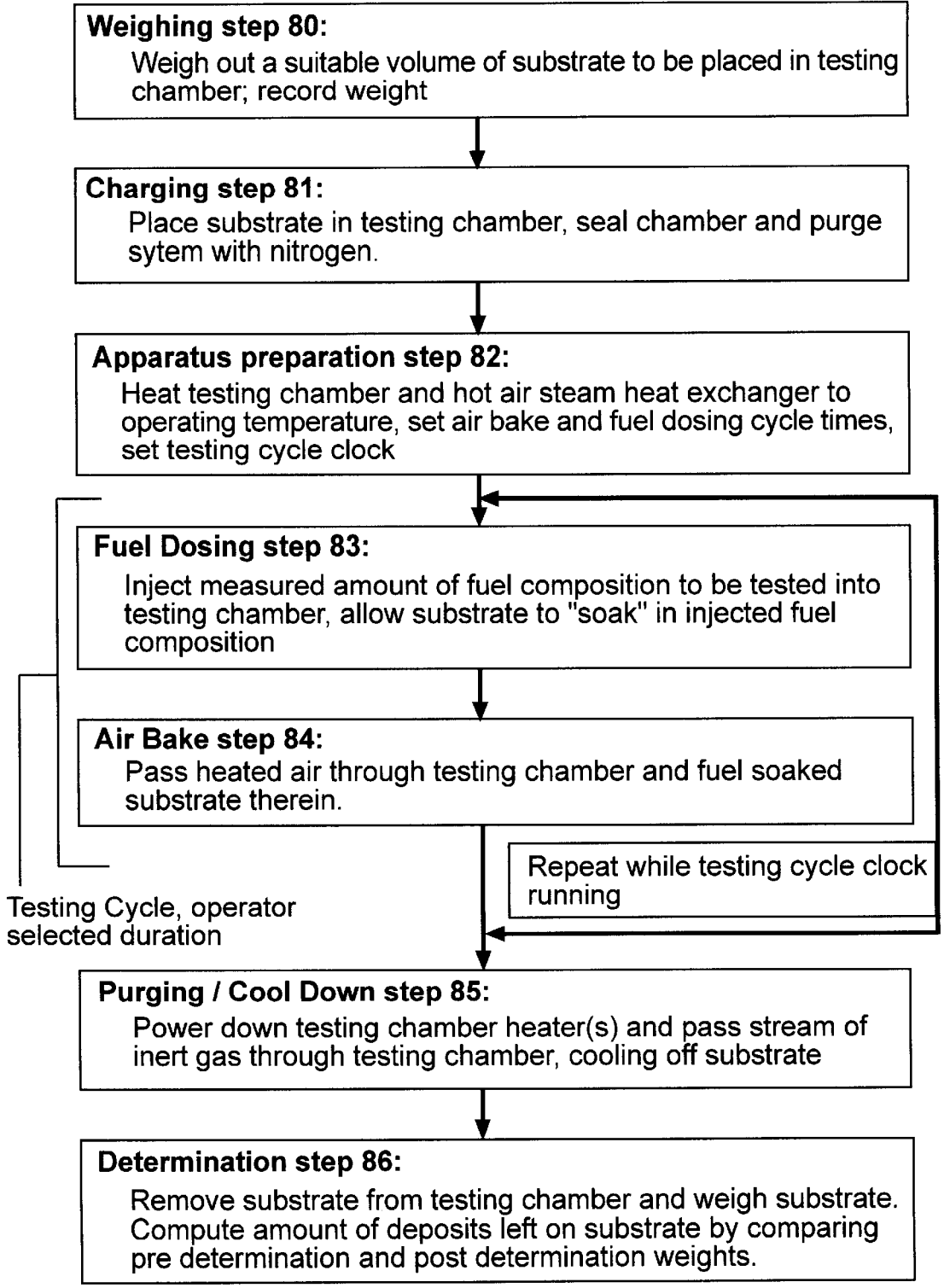
FIG. 8 is a block diagram of the steps carried out in using subject apparatus to determine the propensity of a fuel composition to leave deposits.

With reference to FIG. 8, the method of testing a fuel composition for its propensity to form deposits in the apparatus of the present invention is carried in a number of steps. The first step is a weighing step 80, which requires the operator to weigh out a suitable quantity of substrate material and record its weight.

The next step is the charging step 81, wherein the weighed quantity of substrate material is placed into a test. chamber so that it is in thermal communication with the test chamber and its associated heating and temperature sensing devices. In this step the chamber is sealed and purged out with inert gas.

Step 82, apparatus preparation, follows. Step 82, includes preheating the test chamber to a predetermined temperature, thereby preheating the substrate contained therein to a predetermined temperature and setting the parameters of temperature set point and cycle duration times for the various heated portions of the apparatus and cycles of the testing method. These settings control the engine conditions simulated in the testing apparatus, thus the operator must select the "on state" times of the fuel dosing and air bake cycles and the soak interval prior to the air bake cycle (cycles detailed below). Additionally, the operator must set the testing cycle clock which determines the overall duration of the test.

When the desired temperature is achieved in the substrate, the testing cycle is initiated. The testing cycle includes injecting measured quantities of the fuel composition under test into the test chamber (fuel dosing/soaking step 83) followed by a soaking period during which fuel is distributed through the substrate, and then passing preheated air through the test chamber for a selected period of time (air baking step 84). Thus fuel dosing/soaking step 83 is carried out by actuating, with reference to FIG. 1, fuel flow stop device 121 via control line 153 for a predetermined period of time form 0.062 seconds to 60 seconds, and then permitting the testing chamber to sit static for any selected period of time. Following that, the air bake step is carried out by actuating, with reference to FIG. 1, air flow control device 120 using control line 151 for any selected period of time between 0.62 seconds and 20 hours. At the end of the air baking step, the flow of preheated air through the testing chamber is discontinued by actuating, with reference to FIG. 1, flow stop device 120 to the closed state.

With reference to FIG. 8, fuel dosing/soaking step 83 and air baking step 84 are sequentially repeated while the cycle clock is running. When the testing cycle clock time has elapsed, at the completion of the air bake step in progress or pending, the testing cycle loop is exited and testing chamber purging/cool down step 85 is carried out by purging the testing chamber with nitrogen via, with reference to FIG. 1, purge gas stop flow control device 107 and control line 156, and powering down testing chamber substrate heater 106 to facilitate cooling the testing chamber and therewith the substrate material contained in the testing chamber. Purging is continued until the testing chamber and substrate are brought to a temperature that permits convenient handling of the substrate material.

With reference to FIG. 8, determination step 86 is next carried out, wherein the substrate is removed from the test chamber and weighed, the pre and post test weights being compared and correlated with the results of deposit determinations obtained from tests previously conducted in running compression ignition engines.

In the testing method of the subject invention, gravimetric determination is the preferred manner of determining the amount of deposits which have been formed during the testing cycle, however, it will be appreciated by one skilled in the arts that alternative methods of determining the mass increase in the substrate over the course of the test, such as inertial measuring devices or the change in vibronic frequency of an oscillating substrate may be employed, such devices being familiar to those skilled in the art.

In an alternate embodiment, during the air bake step 84, a predetermined flow of fluid simulating exhaust gas or lubricant vapors may be passed into the test chamber by actuating, with reference to FIG. 1, flow stop device 108 via control line 154. In an alternative embodiment, a plethora of such conduits controlled by such flow stop devices may be employed to provide a wide range of operating parameters during a test. Additional embodiments are possible where other fluids are introduced during any phase of the testing cycle.

It will be appreciated by one skilled in the art that the disclosed testing apparatus may be adjusted, by virtue of its electronic control features, such that a wide range of operating conditions may be simulated by adjusting the temperature and volume of the air stream employed in air bake step 84, the quantity of fuel employed in fuel dosing/soaking step 83, and the temperature of the testing chamber and substrate employed during the testing cycle. Further modification of the testing method is possible in that with suitable electronic controllers, the temperature of the substrate and air used in the air bake step may be dynamically varied during the course of a testing cycle, further tailoring the testing conditions to simulate conditions found in an operating diesel engine.

Figure 9:
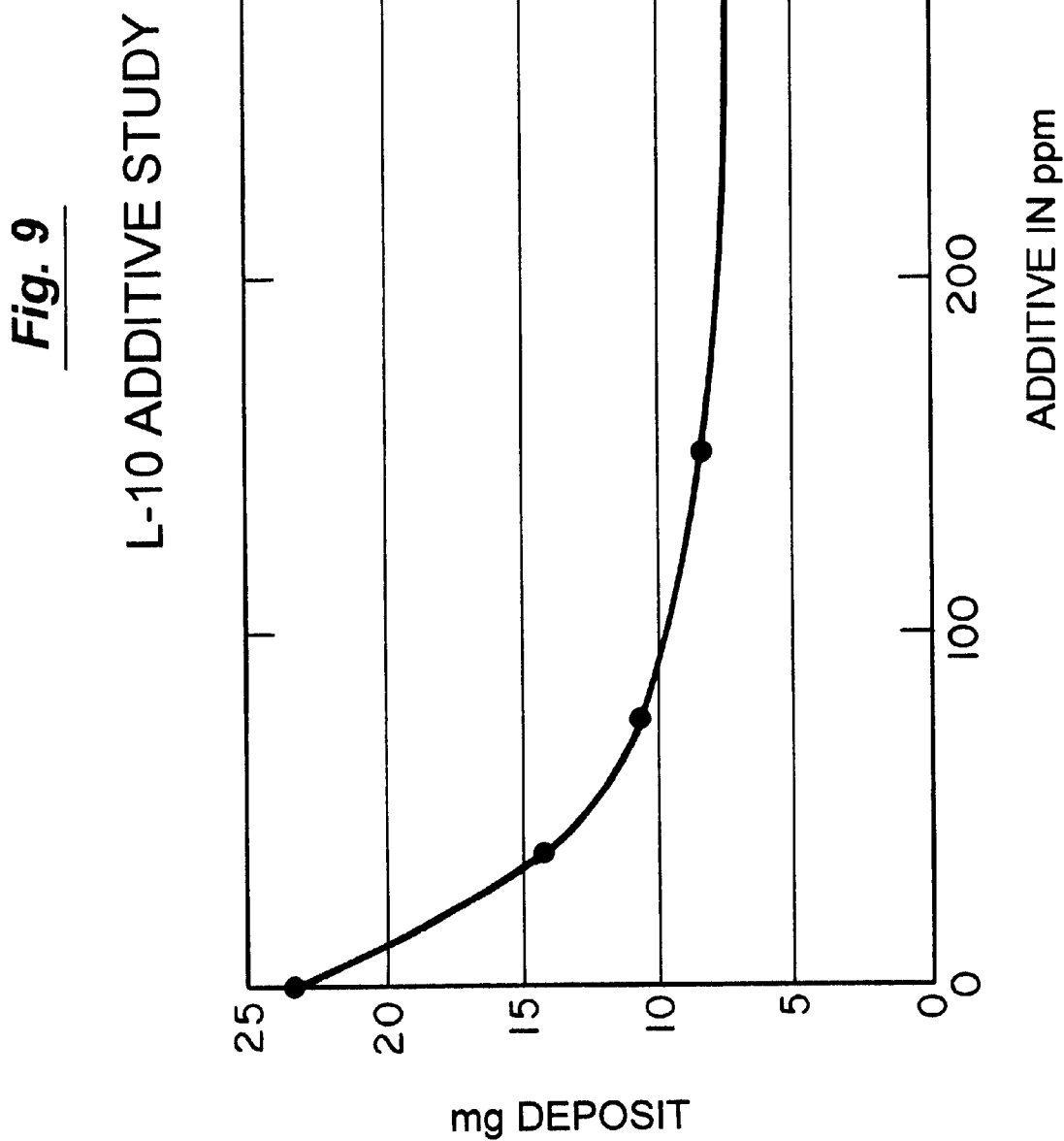
FIG. 9 is a graph illustrating deposit formation as a function of the addition of a typical anti-deposit additive.
Figure 11:
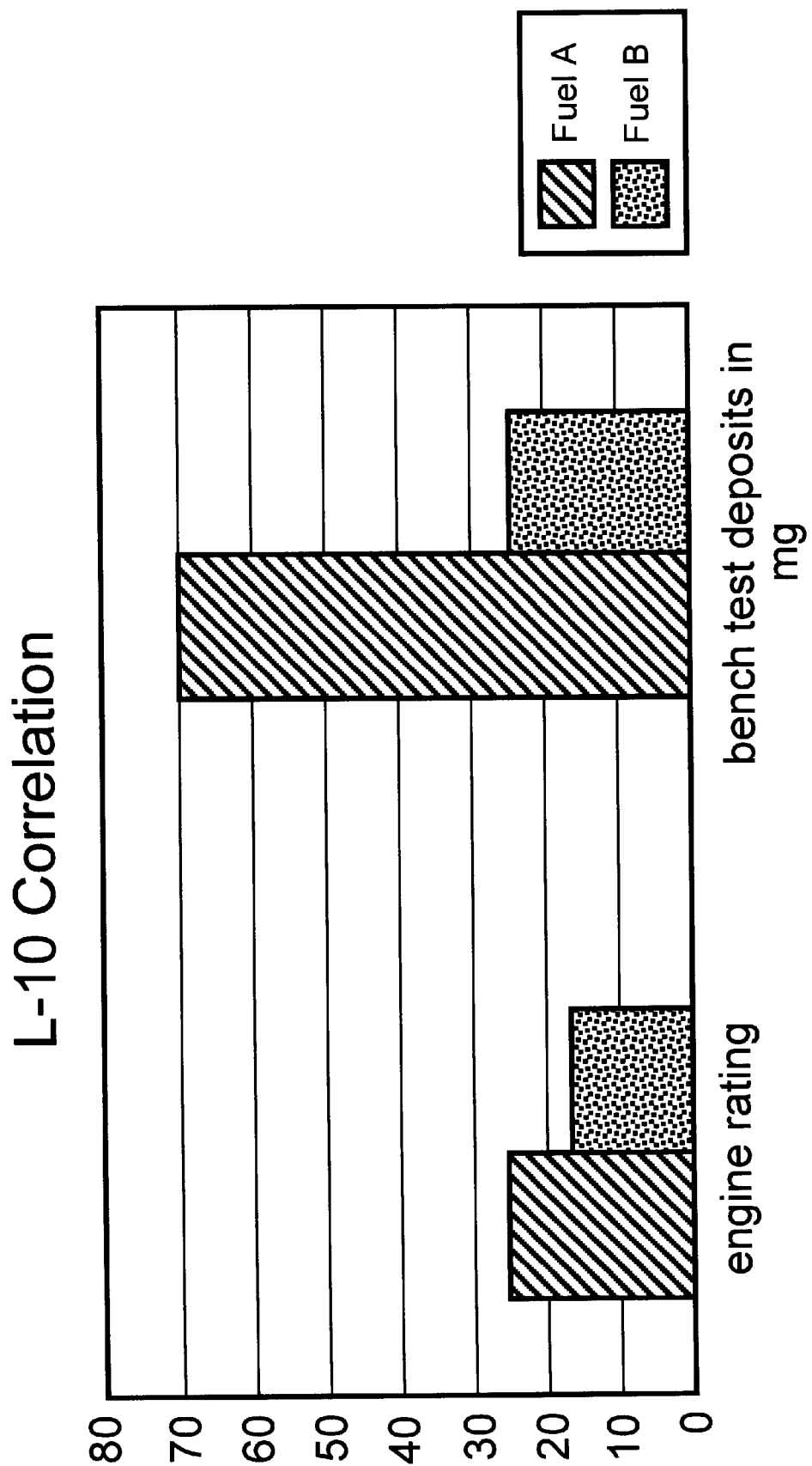
FIG. 11 is a graph illustrating correlation between engine tests and the deposit formation observed in the bench scale deposit testing apparatus.

With reference to FIG. 9, the results of tests conducted in the subject apparatus by the subject method of the instant application are presented showing the effect on deposit formation by addition of an anti-deposit additive to a fuel composition employed in the tests. With reference to FIG. 11, the results of testing in the subject invention testing apparatus are compared with the results obtained from L-10 diesel engine tests, and a close correlation between the two methods is observed.

Although the present invention has been described with reference to preferred embodiments, numerous modifications and variations can be made and still the result will come within the scope of the invention. No limitation with respect to the specific embodiments disclosed herein is intended or should be inferred. Accordingly, patent protection commensurate with this invention is sought as provided by law, with particular reference to the following claims.

What is claimed is:

1. An apparatus for testing the propensity of motor fuel to form deposits in an engine, said apparatus comprising:
    a first chamber having an inlet conduit and an outlet conduit and containing a first heater, whereby a stream of air is heated when passing through said first chamber via said first chamber inlet conduit and said first chamber outlet conduit;
    a first temperature sensor in thermal communication with said stream of air passing through said first chamber outlet conduit;
    a first temperature controller connected to said first temperature sensor and to said first heater whereby the temperature of the air stream passing through said first chamber outlet conduit is maintained at an externally variable predetermined temperature;
    a second chamber having a plurality of inlet conduits and an outlet, at least one of said inlet conduits being a hot air inlet conduit and being connected to said outlet conduit of said first chamber, and at least one of said inlet conduits being a fuel inlet conduit connected to a source of a fuel composition to be tested, said second chamber being adapted to contain a substrate upon which deposits are formed such that said substrate is in thermal communication with the walls of said second chamber;
    an airflow meter interposed between said first chamber outlet conduit and said second chamber air inlet conduit, whereby the volume of air passing into said second chamber may be externally varied between zero and a maximum volume emerging from said first chamber outlet conduit;
    a fuel meter interposed between said second chamber fuel inlet conduit and said fuel source, whereby a measured amount of fuel composition is delivered into said second chamber;
    a second heater in thermal communication with the walls of said second chamber and the substrate contained therein;
    a second temperature sensor in thermal communication with substrate contained in said second chamber;
    a second temperature controller connected to said second temperature sensor and to said second heater, whereby the temperature of the substrate in said second chamber is maintained at an externally variable predetermined temperature;
    said first and second heaters are electric resistance heaters, first and second temperature sensor, and first and second temperature controllers are electrical devices, fuel meter and air flow meter are electrically actuated valves, and wherein said first and second temperature controllers and fuel and air flow meter are connected to a computer whereby the parameters of temperature and delivery volume are controlled by a suitable computer program;
    said second chamber comprises a hollow cylindrical member having two ends, said first end having an opening the width of the inner diameter of the chamber, said second end having a conical taper to an opening of less than the inner diameter of the chamber, and wherein said first end is attached to a first half of a flange sealing mechanism, said first half having an opening coaxial with said cylindrical member, first end of suitable size to permit insertion and removal of substrate material and said outlet opening being fitted with a perforated member of suitable configuration to retain said substrate material within said second chamber, and wherein a second half of a flange sealing material is a blank flange half and is mated to said first half of a flange sealing mechanism, thereby sealing said second chamber.

2. The apparatus of claim 1, wherein said blank flange half comprises a plate containing a sealing face and having at least one passageway through it whereby said passageway effects an inlet conduit for passing fluids into said second chamber when mated to said second chamber.

3. The apparatus of claim 2, wherein said second temperature sensing device comprises at least 2 thermocouples, a first thermocouple being connected to a first channel of said second temperature controller and a second thermocouple connected to a second channel of said second temperature controller such that said first thermocouple is employed as a feedback device to regulate the substrate temperature, and said second thermocouple operates to detect temperatures which a exceed preset maximum, said second temperature control channel supplying electrical signal when an excessive temperature condition is detected.

4. The apparatus of claim 3, wherein at least one second chamber inlet conduit is connected to a source of fire suppressing gas, an electrically operated flow stop device being interposed between said fire suppressing gas source and said second chamber inlet conduit, said computer control device being adapted such that it will actuate said interposed flow stop device upon receiving an electrical signal corresponding to an over-temperature condition being detected by said second channel of said second temperature controller.

5. The apparatus of claim 3, wherein said fuel meter is a fuel injector capable of simulating the fuel delivery in a diesel engine.

6. A method of simulating the conditions in the fuel injectors of an operating diesel engine to determine the deposit forming propensity of diesel fuel, said method comprising the steps of:

placing a preweighed substrate having a suitable surface are and surface finish in a test chamber having at least one inlet and one outlet;

recording a substrate weight;

heating the test chamber and substrate to a predetermined temperature;

carrying out a testing cycle comprising the steps of;
introducing a measured quantity of the fuel to be tested into the test chamber and dispersing it over the substrate contained therein,
soaking the fuel covered substrate at a selected temperature for a selected period of time,
heating a stream of air to a predetermined temperature,
passing the preheated air stream through the test chamber for a selected period of time,
repeating the steps of introducing a measured quantity of fuel, soaking the fuel covered substrate, and passing preheated air through the chamber, said repetition occurring continuously over a selected duration;

discontinuing the steps of the testing cycle and purging inert gas through the test chamber;

cooling the test chamber and thereby the substrate therein to a temperature conducive to handling the substrate;

removing the substrate from the chamber in a manner such that the deposits residing upon the substrate are not disturbed;

weighing the substrate;

calculating an amount of deposits formed on the substrate;

said substrate being composed of stainless ball bearings having approximately ¼ inch diameter and grade 25 hardness.

7. A method of simulating the conditions in the fuel injectors of an operating diesel engine to determine the deposit forming propensity of diesel fuel, said method comprising the steps of:

placing a preweighed substrate having a suitable surface area and surface finish in a test chamber having at least one inlet and one outlet;

recording a substrate weight;

heating the test chamber and the substrate to a predetermined temperature;

carrying out a testing cycle comprising the steps of;
introducing a measured quantity of the fuel to be tested into the test chamber and dispersing it over the substrate contained therein,
soaking the fuel covered substrate at a selected temperature for a selected period of time,
heating a stream of air to a predetermined-temperature,
mixing the heated stream of air with a gaseous stream having the chemical characteristic of diesel exhaust gas,
passing the preheated air simulated exhaust gas mixture through the test chamber for a selected period of time,
repeating the steps of introducing a measured quantity of fuel, soaking the fuel covered substrate, and passing preheated air through the chamber, said repetition occurring continuously over a selected duration;

calculating the amount of deposits formed on the substrate;

said substrate is stainless ball bearings having approximately ¼ inch diameter and grade 25 hardness.

8. An apparatus for testing the propensity of motor fuel to form deposits in an engine, said apparatus comprising:

a first chamber having an inlet conduit and an outlet conduit and containing a first heater, whereby a stream of air is heated when passing through said first chamber via said first chamber inlet conduit and said first chamber outlet conduit;

a first temperature sensor in thermal communication with said stream of air passing through said first chamber outlet conduit;

a first temperature controller connected to said first temperature sensor and to said first heater whereby the temperature of the air stream passing through said first chamber outlet conduit is maintained at an externally variable predetermined temperature;

a second chamber having a plurality of inlet conduits and an outlet, at least one of said inlet conduits being a hot air inlet conduit and being connected to said outlet conduit of said first chamber, and at least one of said inlet conduits being a fuel inlet conduit connected to a source of a fuel composition to be tested, said second chamber being adapted to contain a substrate upon which deposits are formed such that said substrate is in thermal communication with the walls of said second chamber;

an air flow meter interposed between said first chamber outlet conduit and said second chamber air inlet conduit, whereby the volume of air passing into said second chamber may be externally varied between zero and a maximum volume emerging from said first chamber outlet conduit;

a fuel meter interposed between said second chamber fuel inlet conduit and said fuel source, whereby a measured amount of fuel composition is delivered into said second chamber;

a second heater in thermal communication with the walls of said second chamber and the substrate contained therein;

a second temperature sensor in thermal communication with substrate contained in said second chamber;

a second temperature controller connected to said second temperature sensor and to said second heater, whereby the temperature of the substrate in said second chamber is maintained at an externally variable predetermined temperature;

said fuel meter is a fuel injector capable of simulating the fuel delivery in a diesel engine, and the air flow is an electrically actuated diaphragm valve;

at least one of said second chamber inlet conduits is in communication with a groove machined into an inner surface of said second chamber.

* * * * *